United States Patent [19]

Barnes et al.

[11] Patent Number: 4,861,595

[45] Date of Patent: * Aug. 29, 1989

[54] CELLULAR ENCAPSULATION OF BIOLOGICALS FOR ANIMAL AND HUMAN USE

[75] Inventors: Andrew C. Barnes; David L. Edwards, both of San Diego, Calif.

[73] Assignee: Mycogen Corporation, San Diego, Calif.

[*] Notice: The portion of the term of this patent subsequent to Sep. 22, 2004 has been disclaimed.

[21] Appl. No.: 95,749

[22] Filed: Sep. 11, 1987

Related U.S. Application Data

[63] Continuation-in-part of Ser. No. 750,369, Jun. 28, 1985, Pat. No. 4,695,462.

[51] Int. Cl.$^4$ ............................................. A01N 65/00
[52] U.S. Cl. ................................... 424/195.1; 424/93; 424/DIG. 8; 514/2; 514/773; 514/783
[58] Field of Search ................ 424/93, 195.1, DIG. 8; 514/2, 773, 783

[56] References Cited

U.S. PATENT DOCUMENTS 4,265,880 5/1981 Spence et al. .......................... 424/93

FOREIGN PATENT DOCUMENTS 515047 2/1976 Japan .

OTHER PUBLICATIONS

West, A. W., (1984), "Fate of the Insecticidal, Proteinaceos Parasporal Crystal of B. thuringiensis in Soil", Soil Biol. Biochem., 16:357–360.

West, A. W. et al., (1984), "Detection of B. thuringiensis in Soil by Immunofluorescence"; J. of Invertebrate Pathology, 43:150–155.

Arnold, Russell G. (1984) "Microcapsules for New Animal Drugs," Appl. Biochem. Biotechnol., 10:237–243.

Banaker, Umesh V. (1987) "Innovations in Controlled Release," Amer. Pharm. 27:39–42.

Freeman, F. J., Hayward, J. A. and Chapman, D. (1987) "Permeability Studies on Liposomes Formed from Polymerisable Diacetylenic Phospholipids and Their Potential Applications as Drug Delivery Systems," Biochem. Biophys. Acta. 924:341–351.

Friedman, M., Donbrow, M., and Samuelov, Y. (1979) "Placebo Granules as Cores for Timed Release Drug Delivery Systems," J. Pharm. Pharmacol. 31:396–399.

*Primary Examiner*—William R. Dixon, Jr.
*Assistant Examiner*—David M. Brunsman
*Attorney, Agent, or Firm*—Roman Saliwanchik; David R. Saliwanchik

[57] ABSTRACT

A biological delivery system particularly suited for delivery of protein compounds to animals and humans is disclosed. The system uses a producing microbe itself after suitable treatment by chemical and/or physical means. The product being delivered is contained within the treated microbial cell; it is produced intracellularly by a homologous (native) gene.

44 Claims, No Drawings

CELLULAR ENCAPSULATION OF BIOLOGICALS FOR ANIMAL AND HUMAN USE

CROSS REFERENCE TO RELATED APPLICATION

This is a continuation-in-part of copending application Ser. No. 750,369; filed June 28, 1985, now U.S. Pat. No. 4,695,462.

BACKGROUND OF THE INVENTION

Considerable research and development has been applied to delivery of drugs to economically-important animals. Drugs have been formulated in numerous ways for administration, both transdermally and by ingestion. Current reviews are provided by Banaker (Banaker, U. V. [1987] Amer. Pharm. 27:39–42) and by Breimer (Breimer, D. D. [1986] Proc. 3rd Congress European Assoc. for Vet. Pharm. and Toxicol. 75–84). For administration by ingestion, drugs have been incorporated into liposomes (Freeman, F. J., Hayward, J. A. and Chapman, D. [1987] Biochem. Biophys. Acta. 924:341–351), into granules prepared by fluidized bed coating with materials such as ethyl cellulose (Friedman, M., Donbrow, M. and Samuelon, Y. [1979] J. Pharm. Pharmacol. 31: 396–399), and into various types of microcapsules (Arnold, R. G. [1984] Appl. Biochem. Biotechnol. 10: 237–243).

A consequence of the development of this technology is the considerable expense incurred in processing drugs into an appropriate form for delivery. Polypeptide (protein) drugs are unusually difficult to deliver because they are relatively labile and can be degraded by the host before they can be delivered to their site of action, such as intestines, stomachs, etc.

There is a continuous need for economical and efficient drug delivery systems for both animals and humans.

BRIEF SUMMARY OF THE INVENTION

The subject invention concerns a biological delivery system particularly suited for delivery of protein compounds to animals and humans. More specifically, the invention concerns the use of treated, substantially intact, microbial cells as a delivery system of protein compounds to animals and humans. The microbial cells initially produce a protein intracellularly via a homologous (native) gene.

The protein-producing microbe is treated while the cell is substantially intact. Disclosed herein are examples of physical and chemical means which can be used to treat the microbial cell. These examples are not intended to be exhaustive, but merely serve to illustrate the invention.

The crux of the invention is that by manipulation of the microbial cell treatment process it is possible to produce a treated microbial cell which will be non-proliferative, i.e., will not replicate, and will have a stabilized cell wall which breaks down in the desired area of the animal or human body, e.g., intestine, third stomach, etc., or within the digestive system of the target pest. Thus, the invention concerns a "timed or targeted release" of produced protein in the animal or human body, or in the target pest.

The invention process differs from the use of synthetic materials which have found extensive use in encapsulating medicinal compounds. Advantageously, the subject invention uses the protein-producing microbial cell itself as the delivery system after the cell is suitably treated. Thus, no purification of the produced protein compound is necessary. Production of the desired compound is achieved by standard large-scale fermentation. In addition, by choice of the proper microorganism, the host cells, e.g., yeast cells, can serve as a nutrient source for the animal.

Detailed Disclosure of the Invention

In accordance with the subject invention, a novel protein and/or drug delivery system is provided. The subject invention involves treating microbes to prolong the activity of the desired compound produced in the cell when the cell is delivered to the animal or human. The resulting product retains the integrity and biological activity of the desired compound.

Any protein, polypeptide, amino acid or compound producible by microbial means can be the starting material for the invention process. Examples of such microbially-produced products are growth hormones, enzymes, nematocides, insecticides, anti-infectives, antivirals, antifungals, and the like.

Illustratively, a wide variety of proteins can be produced which will be characterized by being capable of being produced intracellularly, particularly in a unicellular microorganism host, such as prokaryotes, e.g., bacteria; or eukaryotes, e.g., fungi, exemplified by yeast and filamentous fungi, such as Neurospora and Aspergillus; or protists, such as amoebas, protozoa, algae, and the like.

The protein can be a nematocide produced by a *Bacillus thuringiensis* (B.t.) microorganisms. In such a case the B.t. microbe can be treated in accord with the process disclosed herein to provide an economical and efficient delivery system to treat animals and humans afflicted with nematodes. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, Caenorhabditis, and Parascaris. Certain of these, such as Nematodirus, Cooperia, and Oesophagostomum, attack primarily the intestinal tract, while others, such as Dictyocaulus are found in the lungs. Still other parasites may be located in other tissues and organs of the body.

Products encapsulatable by the process of the subject invention, advantageously, can be targeted to be released at a specific site in the animal or human host, or in the target pest. This "targeting of release" can be achieved by the nature of treatment of the microbial cell containing the desired product. For example, certain products, advantageously, are released in the animal digestive system. Examples of such products are growth hormones, therapeutic agents, intestinal parasite pesticides, and the like. Other products, advantageously, will pass through the animal or human host substantially intact and maintain the encapsulated protein substantially in the active form in the excrement or fecal matter. This targeted release would, for example, limit the proliferation of flies in such waste matter.

Microbes suitable for treatment in the subject invention can be any microbe which itself would not be toxic to the animal or human host when administered in the treated form. It should be recognized that the treatment of the microbe will render the microbe non-proliferative. At any rate, a large number of microbes are known which are not toxic per se to animals and humans.

Illustrative host cells may include either prokaryotes or eukaryotes, normally being limited to those cells which do not produce substances toxic to animals. However, organisms which produce substances toxic to higher organisms could be used, where the toxin is unstable or the level of application sufficiently low as to avoid any possibility of toxicity to an animal host.

When the treated microbe, e.g., B.t. microbe, is administered as a component of the feed of animals, or dispersed or suspended in the drinking water, compositions are provided in which the encapsulated B.t. microbe is intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the treated B.t. microbe is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible beam mill feed, soya grits, crushed limestone and the like.

In addition to having anthelminthic activity within the digestive tract of animals, appropriately treated B.t. isolates will pass through the animals' digestive tract and thereby provide additional control of nematode larvae which hatch and multiply in the feces.

The protein which is produced in the host cell may be a polypeptide produced in active form or a precursor or proform which requires further processing for activity. Thus, the gene may encode an enzyme which modifies a metabolite to produce a protein composition.

Treatment of the microbial cell, e.g., B.t. cell, can be by chemical or physical means, or by a combination of chemical and/or physical means, so long as the technique does not deleteriously affect the properties of the protein, nor diminish the cellular capability of protecting the protein. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the protein produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to premature breakdown in the animal or human host. Where the protein is in a proform, the method of inactivation should be selected so as not to inhibit processing of the proform to the mature form of the protein by the animal or human host. For example, formaldehyde will cross-link proteins and could inhibit processing of the proform of a protein. The method of inactivation or killing retains at least a substantial portion of the bioavailability or bioactivity of the protein.

The cellular host may be grown in any convenient nutrient medium. These cells may then be harvested in accordance with conventional ways and modified in the various manners described herein. Alternatively, the cells can be treated prior to harvesting.

Following are examples which illustrate procedures, including the best mode, for practicing the invention. These examples should not be construed as limiting.

EXAMPLE 1

Culturing B.t. isolates prior to treatment

A subculture of B.t. isolate can be used to inoculate the following medium, a peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. cells from the above fermentation can be isolated prior to cell lysis by procedures well known in the art. A frequently-used procedure is to subject the harvested fermentation broth to separation techniques, e.g., centrifugation.

Examples 2 and 3, following, are presented to show that gamma radiation from a $^{60}$Cobalt source does not adversely affect the nematocide activity of the B.t. isolates. Though spores and protein crystals were irradiated, rather than substantially-intact B.t. cells, it is expected that similar results would be realized when substantially-intact cells are treated with $^{60}$Cobalt.

EXAMPLE 2

Activity of *Bacillus thuringiensis* isolates against *Caenorhabditis elegans* after treatment with gamma radiation A fresh isolate of *C. elegans* was cultured as described by Simpkin and Coles (J. Chem. Tech. Biotechnol. 31: 66–69, 1981) with 5 mg ampicillin/100 ml in STERILIN multiwell plates. Each well contained approximately 150 worms. The B.t. isolates were grown until sporulation was completed. Samples in fermentation broth were then irradiated with 10 Kilograys of gamma radiation from a $^{60}$Cobalt source. Under these conditions no viable spores or cells remained. One ml aliquots of B.t. samples were centrifuged at 11,000 xg/10 min and the supernatant removed. Pellets were washed twice in nematode washing buffer (Brenner, S. Genetics 77: 71–94, 1974) and resuspended in one ml buffer. Aliquots of supernatant or resuspended pellet material were added to suspensions of worms and incubated at 20° C. for 7 days, after which the wells were observed and the number of live worms relative to controls containing aliquots of *Bacillus subtilis* cultures was noted. All experiments were done in duplicate. The results are as follows:

| Strain | Activity |
|---|---|
| Control (*B. subtilis*) | All worms active |
| *B.t.* PS-11 0.1 ml supernatant | Many active worms |
| 0.5 ml supernatant | Some active worms |
| 0.1 ml pellet | Few active worms |
| 0.5 ml pellet | No live worms |
| *B.t.* PS-33F2 0.1 ml supernatant | Many active worms |
| 0.5 ml supernatant | Many active worms |
| 0.1 ml pellet | <1% live worms |
| 0.5 ml pellet | No live worms |
| *B.t.* PS-52A1 0.1 ml supernatant | Many active worms |
| 0.5 ml supernatant | Many active worms |
| 0.1 ml pellet | No live worms |
| 0.5 ml pellet | No live worms |
| *B.t.* PS-63B 0.1 ml supernatant | Many active worms |
| 0.5 ml supernatant | Many active worms |
| 0.1 ml pellet | Many active worms |
| 0.5 ml pellet | Few active worms |
| *B.t.* PS-69D1 supernatant | Not assayed |
| 1.0 ml pellet | No live worms |

EXAMPLE 3

Activity of delta endotoxin preparations of *Bacillus thuringiensis* isolates after treatment with gamma radiation on *C. elegans*

Isolates of *Bacillus thuringiensis* were grown until sporulation was completed. Delta endotoxin crystals were prepared from these cultures on sodium bromide gradients as described by Pfannenstiel et al. (Pfannenstiel, M. A., Ross, E. J., Kramer, V. C. and Nickerson, K. W. 1984. FEMS Microbiol. Lett. 21: 39–42). The toxin crystal preparations were then irradiated with 10 Kilograys of gamma radiation from a $^{60}$Co source to inactivate any bacterial spores that may have been in the preparation. The protein content of the crystal preparations was determined by the method of Lowry (Lowry, O. H., Roseborough, N. J., Farr, A. L. and Randall, R. J., J. Biol. Chem. 193: 265–275, 1951) and 100 μg of material was added to the test wells. All experiments were done in duplicate. The results are as follows:

| Strain | Activity |
|---|---|
| *B.t.* PS-17 | No live worms |
| *B.t.* PS-33F2 | <1% live worms |
| *B.t.* PS-52A1 | <1% live worms |
| *B.t.* PS-63B | No live worms |
| *B t.* PS-69D1 | <1% live worms |

EXAMPLE 4

Treated *Bacillus thuringiensis* isolates

Substantially intact cells of the B.t. isolates of Example 2 are treated with Lugol's iodine. The treated cells can be utilized as a feed supplement with nematocidal properties. By varying the treatment conditions the B.t. cells can be made to substantially break down in the instestine, or, if desired, pass through the animal substantially intact and be excreted to act as a nematocide in the feces.

EXAMPLE 5

Treated *Bacillus thuringiensis* var. israelensis (B.t.i.)

Substantially intact cells of a B.t.i. microbe, of which many are publicly known and available, are treated with Lugol's iodine. The treated cells can be utilized as a feed supplement with dipteran activity, e.g., activity against flies. The treatment of the cells is such that a substantial fraction of the treated B.t.i. cells pass through the animal and are excreted in the feces to control flies attracted to the feces.

Likewise, appropriately treated B.t.i. cells also can be deployed on lakes, rivers, ponds and other areas infested with mosquitos and/or flies.

The B.t. isolates disclosed herein are available from the Agricultural Research Service Patent Culture Collection (NRRL), Northern Regional Research Center, 1915 North University Street, Peoria, Ill. 61604 USA.

| Culture | Repository No. | Deposit Date |
|---|---|---|
| *B.t.* strain PS-17 | NRRL B-18243 | July 28, 1987 |
| *B.t.* strain PS-33F2 | NRRL B-18244 | July 28, 1987 |
| *B.t.* strain PS-52A1 | NRRL B-18245 | July 28, 1987 |
| *B.t.* strain PS-63B | NRRL B-18246 | July 28, 1987 |
| *B.t.* strain PS-69D1 | NRRL B-18247 | July 28, 1987 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by govermental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any

We claim:

1. A microbial delivery means for use in animals or humans consisting essentially of a microbe comprising a desired intracellular compound produced by a homologous gene, said microbe, while substantially intact, treated with chemical or physical means sufficient to render said microbe non-proliferative, and stabilize the microbial cell without significant loss of activity of the intracellular compound.

2. The microbial delivery means, according to claim 1, wherein said microbe is a prokaryote or a eukaryote.

3. The microbial delivery means, according to claim 2, wherein said eukaryote is a yeast.

4. The microbial delivery means, according to claim 2, wherein said prokaryote is a *Bacillus thuringiensis*.

5. The microbial delivery means, according to claim 4, wherein said *Bacillus thuringiensis* is a nematocide- or insecticide-producing strain of *Bacillus thuringiensis*.

6. The microbial delivery means, according to claim 5, wherein said nematocide-producing strain of *Bacillus thuringiensis* is selected from the group consisting of B.t. PS-17, B.t. PS-33F2, B.t. PS-52A1, B.t. PS-63B, and B.t. PS-69D1.

7. The microbial delivery means, according to claim 6, wherein said nematocide-producing strain of *Bacillus thuringiensis* is B.t. PS-17.

8. The microbial delivery means, according to claim 6, wherein said nematocide-producing strain of *Bacillus thuringiensis* is B.t. PS-33F2.

9. The microbial delivery means, according to claim 6, wherein said nematocide-producing strain of *Bacillus thuringiensis* is B.t. PS-52A1.

10. The microbial delivery means, according to claim 6, wherein said nematocide-producing strain of *Bacillus thuringiensis* is B.t. PS-63B.

11. The microbial delivery means, according to claim 6, wherein said nematocide-producing strain of *Bacillus thuringiensis* is B.t. PS-69D1.

12. The microbial delivery means, according to claim 1, wherein said chemical means is Lugol's iodine.

13. The microbial delivery means, according to claim 1, wherein said physical means is short wavelength radiation less than 400 nm.

14. The microbial delivery means, according to claim 13, wherein said short wavelength radiation less than 400 nm is gamma radiation or radiation from $^{60}$Cobalt.

15. The microbial delivery means, according to claim 1, wherein said intracellularly-produced compound is a protein or polypeptide.

16. The microbial delivery means, according to claim 15, wherein said protein or polypeptide is a toxin.

17. The microbial delivery means, according to claim 16, wherein said toxin is producible by a *Bacillus thuringiensis* microbe.

18. A process for delivering a compound to an animal or human body which comprises administering to said animal or human body a microbe comprising a desired intracellular compound produced by a homologous gene, said microbe, while substantially intact, treated with chemical or physical means sufficient to render said microbe non-proliferative, and stabilize the microbial cell without significant loss of activity of the intracellular compound.

19. The process, according to claim 18, wherein said microbe is a prokaryote or a eukaryote.

20. The process, according to claim 19, wherein said eukoryote is a yeast.

21. The process, according to claim 19, wherein said prokaryote is a *Bacillus thuringiensis*.

22. The process, according to claim 21, wherein said *Bacillus thuringiensis* is a nematocide- or insecticide-producing strain of *Bacillus thuringiensis*.

23. The process, according to claim 22, wherein said nematocide-producing strain of *Bacillus thuringiensis* is selected from the group consisting of B.t. PS-17, B.t. PS-33F2, B.t. PS-52A1, B.t. PS-63B, and B.t. PS-69.D1.

24. The process, according to claim 23, wherein said nematocide-producing strain of *Bacillus thuringiensis* is B.t. PS-17.

25. The process, according to claim 23, wherein said nematocide-producing strain of *Bacillus thuringiensis* is B.t. PS-33F2.

26. The process, according to claim 23, wherein said nematocide-producing strain of *Bacillus thuringiensis* is B.t. PS-52A1.

27. The process, according to claim 23, wherein said nematocide-producing strain of *Bacillus thuringiensis* is B.t. PS-63B.

28. The process, according to claim 23, wherein said nematocide-producing strain of *Bacillus thuringiensis* is B.t. PS-69D1.

29. The process, according to claim 18, wherein said chemical means as Lugol's iodine.

30. The process, according to claim 18, wherein said physical means is short wavelength radiation less than 400 nm.

31. The process, according to claim 30, wherein said short wavelength radiation is gamma radiation or radiation from $^{60}$Cobalt.

32. The process, according to claim 18, wherein said intracellularly-produced compound is a protein or polypeptide.

33. The process, according to claim 32, wherein said protein or polypeptide is a toxin.

34. The process, according to claim 33, wherein said toxin is producible by a *Bacillus thuringiensis* microbe.

35. A process for treating an animal or human hosting a nematocide infestation which comprises administering to said animal or human a nematocide compound effective to control said infestation, wherein said nematocide compound is delivered to said animal or human host by a microbial delivery means consisting essentially of a microbe comprising a desired intracellular compound produced by a homologous gene, said microbe, while substantially intact, treated with chemical or physical means sufficient to render said microbe nonproliferative, and stabilize the microbial cell without significant loss of activity of the intracellular compound.

36. The process, according to claim 35, wherein said microbe is a prokaryote or a eukaryote.

37. The process, according to claim 36, wherein said eukaryote is a yeast.

38. The process, according to claim 36, wherein said prokaryote is a *Bacillus thuringiensis*.

39. The process, according to claim 35, wherein said chemical means is Lugol's iodine.

40. The process, according to claim 35, wherein said physical means is short wavelength radiation less than 400 nm.

41. The process, according to claim 40, wherein said short wavelength radiation is gamma radiation or radiation from $^{60}$Cobalt.

42. The process, according to claim 35, wherein said microbial delivery means is used as a feed supplement when treating nematode-infested animals.

43. A feed supplement comprising a microbe comprising a desired intracellular compound produced by a homologous gene, said microbe, while substantially intact, treated with chemical or physical means sufficient to render said microbe non-proliferative, and stabilize the microbial cell without significant loss of activity of the intracellular compound.

44. The feed supplement, according to claim 43, wherein said desired intracellular compound is selected from the group consisting of growth hormones, enzymes, nematocides, insecticides, anti-infectives, antivirals, and antifungals.

* * * * *

UNITED STATES PATENT AND TRADEMARK OFFICE
CERTIFICATE OF CORRECTION

PATENT NO. : 4,861,595

DATED : August 29, 1989

INVENTOR(S) : Andrew C. Barnes, David L. Edwards

It is certified that error appears in the above-identified patent and that said Letters Patent is hereby corrected as shown below:

Column 1:  line 25:  "Samuelon" should read --Samuelov--
Column 3:  line 38:  "beam" should read --bean--
Column 5:  line 31:  "PS-11 0.1 ml" should read --PS-17 0.1 ml--

Signed and Sealed this

First Day of January, 1991

Attest:

HARRY F. MANBECK, JR.

Attesting Officer

Commissioner of Patents and Trademarks